United States Patent [19]

Doughty et al.

[11] 4,066,673

[45] Jan. 3, 1978

[54] PROCESS FOR MAKING QUATERNARY AMINES OF EPICHLOROHYDRIN

[75] Inventors: Joseph B. Doughty, Sullivan's Island, S.C.; Robert E. Klem, Columbia, Md.

[73] Assignee: Westvaco Corporation, New York, N.Y.

[21] Appl. No.: 445,067

[22] Filed: Feb. 25, 1974

[51] Int. Cl.$^2$ .................. C07D 301/24; C07D 301/00
[52] U.S. Cl. ........................... 260/348.13; 260/348.44
[58] Field of Search .................................. 260/348 R

[56] References Cited

U.S. PATENT DOCUMENTS

| | | | |
|---|---|---|---|
| 3,262,916 | 7/1966 | Gaertner | 260/348 R |
| 3,510,246 | 5/1970 | Keen et al. | 8/116.2 |
| 3,649,616 | 3/1972 | Goldstein et al. | 260/233.3 R |

FOREIGN PATENT DOCUMENTS 1,493,519   2/1969   Germany.

OTHER PUBLICATIONS

J. B. Mckelvey et al., Jour. Org. Chem., vol. 25 (1960) pp. 1424–1428.

*Primary Examiner*—Norma S. Milestone
*Attorney, Agent, or Firm*—Richard L. Schmalz; Ernest B. Lipscomb, III

[57] ABSTRACT

The preparation of a 1,2-epoxy propyl trialkylamine chloride in a methanol solution is disclosed. The products are useful for preparing cationic ethers in both aqueous and organic solvent solutions free of inorganic alkalis or salts.

2 Claims, No Drawings

PROCESS FOR MAKING QUATERNARY AMINES OF EPICHLOROHYDRIN

BACKGROUND OF THE INVENTION

1. Field of the Invention

This invention relates to the preparation of a 1,2-epoxy, 3-trialkylamine propyl chloride in a methanol solution.

2. The Prior Art

Epoxy compounds, particularly epichlorohydrin, react with organic hydroxyl containing compounds as follows:

$$CH_2-CHCH_2Cl + ROH \xrightarrow{NaOH} ROCH_2-CHCH_2Cl$$
$$\underset{O}{\diagdown\diagup} \qquad\qquad\qquad \underset{OH}{|}$$

The epoxy compound may be converted to chlorohydroxyl propyl chlorides as:

$$CH_2-CHCH_2Cl + HCl \diagup^{CH_2OHCHClCH_2Cl \quad [A]}_{\diagdown CH_2ClCHOHCH_2Cl \quad [B]}$$

and the mixed hydroxy chlorides reacted with organic hydroxyl compounds as:

$$[A] \text{ or } [B] + ROH \xrightarrow{NaOH} ROCH_2CHCH_2Cl$$
$$\underset{OH}{|}$$

Epichlorohydrin or the chlorohydroxyl propyl chlorides will react with trialkylamines to form the respective quaternary chlorides:

$$CH_2-CHCH_2N(R')_3Cl \qquad [1]$$
$$\underset{O}{\diagdown\diagup}$$

$$CH_2OHCHClCH_2N(R)_3Cl$$
$$\text{or} \qquad\qquad\qquad [2]$$
$$CH_2ClCHOHCH_2N(R)_3Cl$$

Utilization has been made of these reactions to form quaternary amines of hydroxyl containing compounds. Generally, reagents [1] or [2] above are made in aqueous solutions and used as such. These quaternary materials are reacted with the hydroxyl compounds in water in the presence of alkali, usually sodium hydroxide to give the required quaternary amine:

$$ROCH_2CHCH_2N(R')_3Cl \qquad [3]$$
$$\underset{OH}{|}$$

Perhaps, the greatest commercial use of these reactions is in the manufacture of cationic starches. Such a process is disclosed in U.S. Pat. No. 2,876,217. In this process, trimethylamine or other trialkylamine is added to epichlorohydrin in aqueous solution. The solution is concentrated under a vacuum, and this concentrate is added to an alkaline aqueous slurry of starch. The reaction mass is neutralized with acid and the cationized starch recovered. A related process is disclosed in two more recent patents, U.S. Pat. No. 3,346,563 and U.S. Pat. No. 3,532,751. In these processes, alkyl chloride is reacted with a trialkylamine as:

$$CH_2=CHCH_2CL +$$
$$N(R)_3 \rightarrow CH_2=CHCH_2N(R)_3CL \qquad [C]$$

The alkyl amine chloride [C] is then reacted in chlorine water as:

$$[C] + HOCl \diagup^{CH_2OHCHClCH_2N(R)_3Cl}_{\diagdown CH_2ClCHOHCH_2N(R)_3Cl} \qquad [D]$$

The mixed chlorohydroxyl propyl trialkylamines (usually the trimethylamine) in aqueous solution are then reacted with an alkaline slurry of starch to form the cationic starch. Aqueous solutions of about 50% active chlorohydroxyl propyl trimethylamine chloride are commercially available for use as quaternizing agents.

All of the above quaternizing reagents and procedures are in aqueous solution and require alkali to become effective. The mixed chlorohydroxyl amine chlorides available have impurities such as OH or tripropyl chlorides, inorganic salts, di-chloropropanol and some alcohols. Reactions of this material with water insoluble materials are slow, and the many impurities must be removed by tedious separations and water washes.

It is, therefore, the general object of this invention to provide a process for preparing a 1,2-epoxy propyl trialkylamine chloride in methanol.

Other objects, features and advantages of this invention may be seen in the following detailed description.

DETAILED DESCRIPTION OF THE INVENTION

It has now been found that a useful quaternizing compound, 1,2-epoxy propyl trialkylamine chloride, $$(CH_2-CHCH_2N(CH_3)_3Cl,$$
$$\underset{O}{\diagdown\diagup}$$

can be readily made in methanol solution. This alcohol solution is stable; the quaternized epoxy material is formed in nearly stoichiometric amounts of the trialkylamine and epichlorohydrin.

The trialkylamines contemplated for use in this process include, among others, trimethylamine and triethylamine.

To make 1,2-epoxy propyl trimethylamine chloride, first epichlorohydrin is dissolved in methanol and chilled. To this solution is slowly added a stoichiometric amount of trialkylamine in methanol. To achieve a high yield of the quaternizing compound, the reaction is carried out between 0° and 60° C. preferably 0° to 25° C. The methanol generally comprises 5% to 70% by weight of the total, and both the epichlorohydrin and trimethylamine may be dissolved therein. At 0° C. to 40° C. the reaction is fairly rapid; and with 5% to 50% by weight methanol, the quaternizing compound is complete in less than two hours. Using this process, undesirable side reactions and impurities are eliminated, as well as, the need to use alkali.

The preparation of this material and its stability in methanol is unexpected, for when trimethylamine and epichlorohydrin are mixed in isopropyl or ethyl alcohols, a precipitate forms which is not an effective quaternizing agent. Such products are not well characterized. Reactions of the trimethylamine and epichlorohydrin in other solvents such as acetone, ethyl acetate, ether, and hexane also give high yields of these unreactive adducts. Near 100% of the trimethylamine and epichlorohydrin is recovered as the insoluble solids from these latter alcohols.

The practice of this invention may be seen in the following examples:

EXAMPLE 1

Epichlorohydrin, 20 ml (23 grams or 0.25 mole) was dissolved in 29.2 ml (23 grams) of methanol. This solution was chilled to below 5° C. in an ice water bath. To this cold solution was added 59 grams of a 25% solution of trimethylamine in methanol over a period of two hours. The solution was allowed to come to room temperature and stored for about two weeks. The sample of the solution was analyzed for ionizable chlorine. The results showed over 94% of the chlorine in the mix was in the ionic form, showing that reaction of the trimethylamine and epichlorohydrin was of 92% complete in forming the quaternary compound.

EXAMPLE 2

A solution of 20 ml (23 grams or 0.25 mole) of epichlorohydrin and 29.2 ml (23 grams) of methanol was prepared. This solution was chilled to 5° C. or below in an ice water bath. To the cold solution was added 21.4 ml (14.8 grams or 0.25 mole) of liquid trimethylamine which had been chilled to below 5° C. The total mix was stirred in an ice water bath for nearly two hours and then the whole allowed to come to room temperature. Samples of this mix which were over a week old show over 95% of the chlorine in an ionizable form, thus indicating 95% or more reaction to form the respective quaternary compound.

EXAMPLE 3

A reaction mixture was prepared as described in Example 1. To this mixture which had been standing three days at room temperature was added 65.5 grams (0.25 mole) of dodecyl phenol. The whole was heated in a water bath with stirring for five hours at 45° to 55° C. Analyses of a sample of this whole reaction mix for solids in a Cenco-Moisture Balance (Central Scientific Company, Chicago, Illinois) was found to be 60% indicating near 100% reaction. Samples of this material were tested as an emulsifier for asphalt in water and as little as 0.3% was shown to be effective.

EXAMPLE 4

To illustrate the use of the 1,2-epoxy propyl trialkalamine chloride in a methanol solution in the manufacture of a cationic starch, unmodified potato starch was jet cooked (230° F.) with a P & F continuous jet cooker. After adjusting starch solution to 6% solids, 300 grams of the starch solution were placed in round-bottom flask; and solution was held at 50° C. while being continuously stirred. Four grams of the quaternary compound described in Example 1 were added to the starch solution, and pH of the mixture was raised to pH 11 with sodium hydroxide. After 4 hours under the above conditions, reaction mixture was neutralized to pH 6–7. Intrinsic (alkaline) viscosity was determined to be 254 dl/g. Starch was extracted, dried and percent nitrogen content was determined to be 0.20%.

The cationic starch was added to a 1.5% solids slurry consisting of 84.2% pulp and 15.8% filler clay. Addition rate was 1% on weight of pulp and filler clay. A series of handsheets were made with the above mixture of pulp, filler clay and starch. Average percent first pass filler retention was 79.1%.

While the invention has been described and illustrated herein by reference to various specific materials, procedures, and examples, it is understood that the invention is not restricted to the particular materials, combination of materials, and procedures selected for the purpose. Numerous variations of such details can be employed, as will be appreciated by those skilled in the art.

What is claimed is:

1. In a process for preparing a 1,2-epoxy propyl trialkylamine chloride, the improvement which comprises; reacting epichlorohydrin in a methanol solution with a stoichiometric amount of trialkylamine at a temperature between 0° and 60° C., said methanol being about 5% to 70% by weight of the total.

2. A process according to claim 1 in which the trialkylamine is trimethylamine.

* * * * *